United States Patent [19]

Nakai et al.

[11] Patent Number: 5,093,366

[45] Date of Patent: Mar. 3, 1992

[54] NOVEL CINNAMOYLAMIDE DERIVATIVES

[75] Inventors: Hisao Nakai; Hiroshi Terashima, both of Takatsuki; Yoshinobu Arai, Mishima, Japan

[73] Assignee: Ono Pharmaceutical Co., Ltd., Osaka, Japan

[21] Appl. No.: 691,509

[22] Filed: Apr. 25, 1991

Related U.S. Application Data

[60] Division of Ser. No. 572,341, Aug. 24, 1990, Pat. No. 5,037,852, which is a continuation of Ser. No. 191,194, May 6, 1988, abandoned.

[30] Foreign Application Priority Data

May 7, 1987 [JP] Japan ............................. 62-109722

[51] Int. Cl.$^5$ ................................. A61K 31/195
[52] U.S. Cl. ..................... 514/563; 562/441; 562/455
[58] Field of Search ............... 562/441, 455; 514/563

[56] References Cited

U.S. PATENT DOCUMENTS 4,026,896  5/1977  Harita et al. .................... 424/282

FOREIGN PATENT DOCUMENTS

| 173516 | 3/1986 | European Pat. Off. |
| 291247 | 11/1988 | European Pat. Off. |
| 2515914 | 11/1975 | Fed. Rep. of Germany |
| 62-116657 | 6/1985 | Japan |
| 62-198653 | 9/1987 | Japan |

*Primary Examiner*—Bruce Gray

[57] ABSTRACT

A cinnamoylamide derivative of general formula:

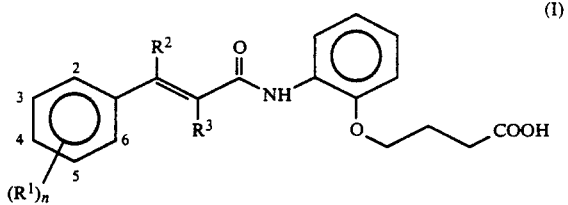

(I)

[wherein,
(i) in case that $R^2$ represents a methyl group and $R^3$ represents a hydrogen atom,
$(R^1)_n$ represents a group selected out of
3-pentyl group,
4-pentyl group,
4-neopentyl group,
4-(2-ethylbutyl) group,
4-(2-methylpentyl) group,
2-fluoro-4-pentyloxy group,
4-butylthio group,
4-cyclobutylmethyl group,
4-cyclohexylmethyl group,
4-(4-phenylbutyl) group and
4-phenoxy group, and
(ii) in case that $R^2$ represents a hydrogen atom and $R^3$ represents a methyl group,
$(R^1)_n$ represents a group selected out of
3-pentyl group and
4-penethyl group.]

or non-toxic salts thereof possess an inhibitory activity on 5α-reductase, and therefore be useful for treating and/or preventing agent for alopecia, acnes or prostatic hyperfrophy.

4 Claims, No Drawings

NOVEL CINNAMOYLAMIDE DERIVATIVES

This is a division of application Ser. No. 07/572,341, filed Aug. 24, 1990, U.S. Pat. No. 5,037,852 which in turn is a continuation of application Ser. No. 07/191,194, filed May 6, 1988, now abandoned.

DESCRIPTION

SUMMARY

This invention is related to novel cinnamoylamide derivatives of the following general formula:

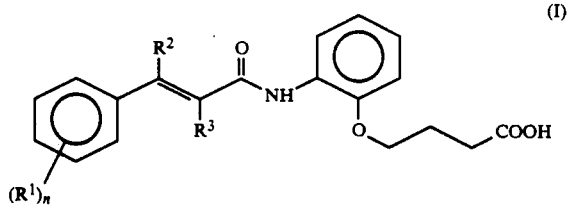

(wherein all of the symbols are the same measuring as hereafter defined.) and inhibitory agents on 5α-reductase containing them as active ingredient.

BACKGROUND

So far, many theories are exposited such as (1) imbalance of hormones, (2) genetics, (3) circulatory failure, (4) nutrition, as the origin of androgenic alopecia.

And it has been also suggested that testosterone (androgenic hormone) played an important role on the generation of hairs.

The theory of Adachi at al in which the relation between testosterone and androgenic alopecia is proved by biochemical experiments, is as follows:

i) first, testosterone biosynthesized in testis is converted into dihydrotestosterone by 5α-reductase existed in hair follicle, sebaceous gland etc. at head.

ii) dihydrotestosterone reduces the activities of adenyl cyclase remarkably.

iii) it decreases cyclic-AMP in cells.

iv) last, it induces lowering of energy generation of hairs and limbus and supressing of protein synthesis (See Biochem. Biophys. Res. Commun., 41, 884 (1970)

According to the theory it is thought that, at the results of the series of the phenomena, hairs in the growing phase shift to the resting phase, the terminal hairs change to the soft hairs, and the androgenic alopecia develops in the end.

A report by H. V. Schweikert supports this theory that large quantities of metabolites by 5α-reductase such as dihydro testosterone etc. in hair follicles of androgenic alopecia-patient exist more than that in females or healthy male. (See J. Clin. Endocr., 38, 811 (1974)

It was reported that dihydrotestosterone converted from testosterone by 5α-reductase also plays in an important physiological role in the generate of acnes (acne, pimple etc.) other than androgenic alopecia. J. B. Hay et al reported that the metabolism of testosterone by 5α-reductase was enhanced in the affected part of acne aggravated, from the study in the flux between affected skin of acne-patient and healthy skin (See Br. J. Dermatol., 91, 123 (1974)).

G. Sansone et al found that synthetic ability of dihydrotestosterone from testosterone developed from two to twenty times in the affected part of acne-patient compared to that in healthy man, they suggested that dihydrotestosterone generated by 5α-reductase greatly relates to the generation or aggravation of acne (See J. Invest. Dermatol., 56, 366 (1971)).

And, dihydrotestosterone is related to the hypertrophy of prostate. Cowan et al reported that much dihydrotestosterone existed in the prostate of prostatic hypertrophy-patient (See J. Steroid Biochemistry, 11, 609 (1979)). Recently, it was known that activity of 5α-reductase in prostate of prostatic hypertrophy-patient aggravated abnormally (See J. Clinical Endocrinol and Metabolism, 56, 139 (1983)).

From those informations it has been clear that dihydrotestosterone plays an important role in the generation and development of prostatic hypertrophy.

PRIOR ARTS AND COMPARISON WITH THEM

On the above background, recently, researches and developments of 5α-reductase inhibitors are carried out energetically and they are mainly steroids or derivatives thereof.

Widespread investigation has been carried out in order to discover compound which have a non-stroidal structure, and possess inhibitory activity on 5α-reductase. The present applicant have found that the above purpose can be accomplished by compounds wherein cinnamic acid or benzoic acids form amides with anilines, and then applicated the patents

[See Japanese Patent Kokai No. 60-97946, Japanese Patent Kokai No. 60-116657, Japanese Patent Kokai No. 60-142936, Japanese Patent Kokai No. 60-142941, Japanese Patent Kokai No. 60-146855, Japanese Patent Kokai No. 61-126061, i.e. the European Patent Publication No. 173516, Japanese Patent Kokai No. 62-198652 and Japanese Patent Kokai No. 62-198653.]

For example, in the specification of Japanese Patent Kokai No. 61-126061, it was described that a very wide range of amide compounds possess inhibitory activity on 5α-reductase. Extracting part related closely to the compounds of the present invention of the general formula (I) in chemical structure from it, it is suggested that the compounds of the general formula:

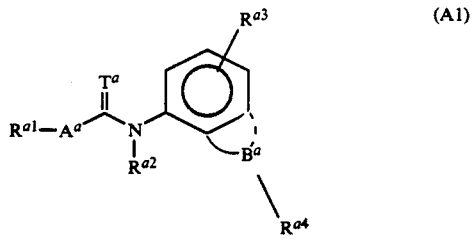

[wherein $A^a$ represents a binylene group unsubstituted or substituted by alkyl group(s) of from 1 to 10 carbon atom(s), $B^a$ represents a bibalent group of —O—CH$_2$— and $R^{a1}$ represents a group of the general formula:

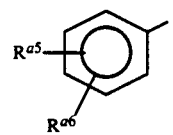

(wherein $R^{a5}$ and $R^{a6}$ represent, independently, a hydrogen atom, halogen atom or alkyl, alkenyl or alkynyl group of from 1 to 20 carbon atom(s) which may be replaced optional carbon atom(s) of from 1 to 5 by an oxygen atom, sulfur atom, halogen atom, nitrogen atom, benzene ring, thiophene ring, naphthalene ring, carbon ring of from 4 to 7 carbon atoms, carbonyl group, carbonyloxy group, hydroxyl group, carboxyl group, azide group or nitro group)

$T^a$ represents a oxygen atom, $R^{a2}$ represents a hydrogen atom, $R^{a3}$ represents a hydrogen atom, $R^{a4}$ represents a group of $-(CH_2)^{ap}-COOR^{a8}$ (wherein ap represents an integer of from 1 to 10, $R^{a8}$ represents a hydrogen atom or an alkyl group of from 1 to 6 carbon atom(s))]

i.e.; the compounds of the general formula:

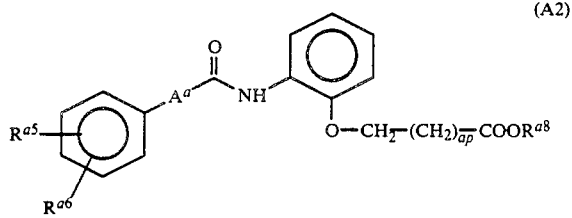

(A2)

(wherein all of the symbols are same meaning as defined hereinbefore.)

On the other hand, the group of compounds which are similar to the compounds of the prevent invention in chemical structure, is disclosed in the specification of Japanese Patent Kokai No. 51-1438 and France Patent Publication No. 2164481.

For example, in the specification of Japanese Patent Kokai No. 51-1438, it is disclosed that the compounds of the general formula

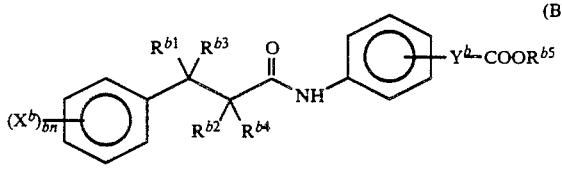

(B)

[wherein $R^{b1}$ and $R^{b2}$ each represent a hydrogen atom or lower alkyl group, $R^{b3}$ represents a chemical bond together with $R^{b4}$.

$X^b$ represents a halogen atom, lower alkyl group, lower alkoxy group or cyclic alkyl group, bn represents an integer of from 1 to 3, $R^{b5}$ represents a hydrogen atom and $Y^b$ represents an oxyalkylene group binding benzene ring via an oxygen atom.]

(the above definitions of symbols are extracted from the original specification) is available as antiallergic agent.

Moreover, in the specification of France Patent Publication No. 2164481, it is disclosed that the compounds of the general formula:

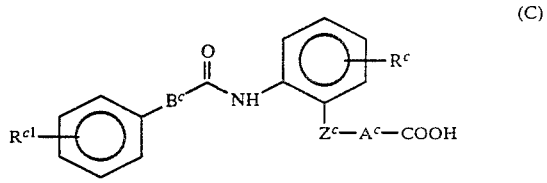

(C)

[wherein $A^c$ represents an alkylene group of from 1 to 3 carbon atom(s), $B^c$ represents a bivalent ethylenic hydrocarbon of from 1 to 5 carbon atom(s), $R^c$ represents a hydrogen atom, $R^{c1}$ represents one or two substituent(s) selected out of an alkyl, cycloalkyl, aryl, aralkyl, halogen, alkoxy, aryloxy and alkylthio group and $Z^c$ represents an oxygen atom]

(the definition of symbols are extracted from the original specification) possess anti-inflammatory and antipyretic action.

PURPOSE OF THE INVENTION

This time, the present inventors have synthesized newly the compounds which belong to the compounds of the general formula (A2) broadly and are not described specifically in the specification of Japanese Patent Kokai No. 61-126061, and confirmed that the compounds possess inhibitory activity on 5α-reductase. As the result, we, the present inventors have found the compounds which possess far more activity than we expected at the beginning and then completed the present invention. It can be quite unexpected that the compounds having remarkably superior activity are contained in the compounds of the general formula (A2)

The compounds of the general formula (I), of the prevent invention are not contained in the general formula (B), and the fact that the compounds of the general formula (B) possess anti-inflammatory activity never quite suggest that the compounds of the prevent invention possess inhibitory activity on 5α-reductase. Examining the specification of France Patent Kokai No. 2164481 in detail, we can understand that only one compound was synthesized in practice. Moreover, the fact that compounds of the general formula (C) possesses anti-inflammatory activity does not quite suggest that the compounds of the present invention possess inhibitory activity on 5α-reductase.

DISCLOSURE OF THE INVENTION

Accordingly, the present invention is related to cinnamoylamide derivatives of the general formula:

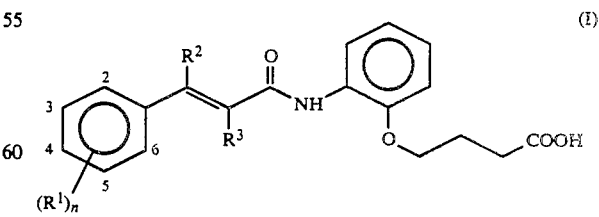

(I)

[wherein, (i) in case that $R^2$ represents a methyl group and R3 represents a hydrogen atom, $(R^1)_n$ represents a group selected out of 3-pentyl group, 4-pentyl group,
4-neopentyl group,
4-(2-ethylbutyl) group,
4-(2-methylpentyl) group,
2-fluoro-4-pentyloxy group,
4-butylthio group,
4-cyclobutylmethyl group,
4-cyclohexylmethyl group,
4-(4-phenylbutyl) group and
4-phenoxy group, and (ii) in case that $R^2$ represents a hydrogen atom and $R^3$ represents a methyl group, $(R^1)_n$ represents a group selected out of
3-pentyl group and
4-phenethyl group], non-toxic salt thereof and inhibitory agents on 5α-reductase containing them as active ingredient.

In the general formula (I), the configuration of a vinylene group which $R^2$ and $R^3$ bond to, is E.

When $(R^1)_n$ represents 4-(2-methylpentyl) group, two optical isomers arise owing to an asymmetric carbon atom in the pentyl group. The present invention includes these two isomers and mixture thereof.

All compounds of the general formula (I) are preferable. Especially, the compounds
[wherein,
(i) in case that $R^2$ represents a methyl group and $R^3$ represents a hydrogen atom,
$(R^1)_n$ represents a group selected out of
3-pentyl group,
4-pentyl group,
2-fluoro-4-pentyloxy group,
4-cyclobutylmethyl group,
4-cyclohexylmethyl group and
4-phenoxy group
(ii) in case that $R^2$ represents a hydrogen atom and $R^3$ represents a methyl group,
$(R^1)_n$ represents a group selected out of
3-pentyl group and
4-phenethyl group]
are preferable. More especially, the compounds wherein $R^2$ represents a methyl group, $R^3$ represents a hydrogen atom and $(R^1)_n$ represents a group selected out of 3-pentyl group, 4-pentyl group and 4-cyclobutylmethyl group are preferable.

NON-TOXIC SALTS

The compounds of the general formula (I), of the present invention may be converted into the corresponding salts by known method. Non-toxic and water soluble salts are preberable. Suitable salts, for example, are follows:
salts of alkaline metal e.g. sodium, potassium,
salts of alkaline earth metal e.g. calcium, magnesium, ammonium salts,
salts of pharmaceutically acceptable amine e.g. tetramethylammonium, triethylamine, methylamine, dimethylamine, cyclopentylamine, benzylamine, phenethylamine, piperidineamine, monoethanolamine, diethanolamine, tris (hydroxymethyl)aminomethane, lysine, arginine, N-methyl-D-glucamine.

PROCESS FOR THE PREPARATION

According to the present invention, the compounds of the general formula (I) of the present invention may be prepared by saponifying the compounds of the general formula:

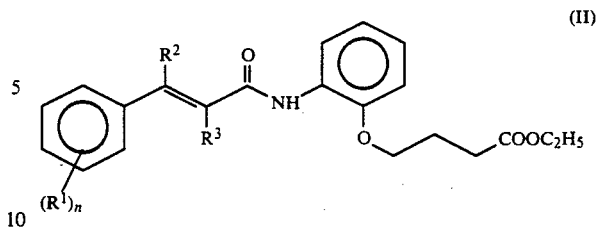

(wherein all of the symbols are the same meaning as hereinbefore defined.)

The saponification is known and it may be carried out, for example, using an aqueous solution of alkali (potassium hydroxide, sodium hydroxide, lithium hydroxide potassium carbonate, sodium carbonate etc.) in a water-miscible organic solvent (tetrahydrofuran (THF), dioxane, ethanol, methanol etc.). The reaction is carried out at a temperature of from $-10°$ C. to $100°$ C.

The compounds of the general formula (II) may be prepared by allowing to react a carboxylic acid of the general formula:

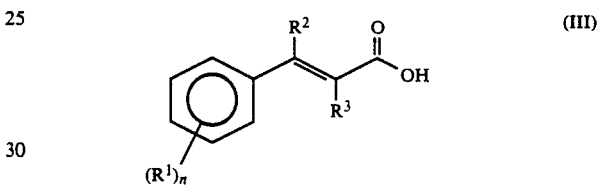

(wherein all of the symbols are the same meaning as defined hereinbefore) with an amine of the general formula:

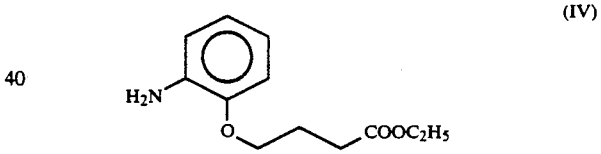

Preparation of amide bond by reacting a carboxylic acid with an amine are known and, for example, are
(A) method using a mixed acid anhydride
(B) method using an acid halide
(C) method using DCC etc.

Described concretely, (A) method using a mixed acid anhydride may be carried out, for example, by reacting, a mixed acid anhydride obtained by acylating a carboxylic acid of the general formula (III) with an acid halide (pivaloyl chloride, tosyl chloride, mesyl chloride, etc.) or an acid derivative (ethyl chloroformate, isobutyl chloroformate, etc.) in the presence of a tertiary amine (pyridine, triethylamine, picoline etc.) in an inert organic solvent (chloroform, methylene chloride, diethyl ether, THF, etc.) or without solvent at from $0°$ C. to $40°$ C., with an amine of the general formula (IV) in an inert organic solvent (described above) at from $0°$ C. to $40°$ C.

(B) Method using acid halide may be carried out, for example, by reacting, an acid halide obtained by treating a carboxylic acid of the general formula (III) with an acid halide (thionylchloride, oxalyl chloride, etc.) in an inert organic solvent (described above) at from $-20°$ C. to refluxing temperature of the solvent used, with an amine of the general formula (IV) in an inert organic solvent (described above) at from 0° C. to 40° C.

(C) Method using a condensing agent such as DCC (dicyclohexylcarbodiimide) may be carried out, for example, by reacting a carboxylic acid of the general formula (III) with an amine of the general formula (IV), using DCC etc., in the presence or absence of tertiary amine (described above), in an inert organic solvent (described above) or without solvent, at from 0° C. to 40° C.

The reactions of (A), (B) and (C) are carried out, preferably, in an atmosphere of inert gas (argon, nitrogen etc) and under anhydrous condition.

Throughout the specification, in each reactions, products may be purified by conventional methods, for example, distillation at atmospheric or reduced pressure, high performance liquied chromatography, thin layer chromatography using silica gel or magnesium silicate or washing or recrystallization. Purification may be carried out after each reactions or a series of reactions.

STARTING MATERIALS

Starting materials and reagents in the prevent invention are known per se or may be prepared by known methods.

For example, a carboxylic acid of the general formula (III) may be prepared by the method described in the specification of Japanese Patent Kokai Nos. 60-97946, 60-116657, 60-142936, 60-142941 and 60-146855.

An amine of the formula (IV) may be prepared by the method described in the specification of Japanese Patent Kokai No. 61-126061.

PHARMACOLOGICAL ACTIVITIES OF THE COMPOUNDS OF THE PRESENT INVENTION

The compounds of the general formula (I) of the present invention possess an inhibitory activity on 5α-reductase and therefore are useful for prevention and/or treatment of diseases resulted from the excess generation of dihydrotestosteron in mammals, especialby human. The diseases such as above, for example, are alopecia e.g. androgenic alopecia, acnes and hypertrophy of prostate.

An inhibitory activity on 5α-reductase of the present invention is confirmed by the screening system described hereafter.

INHIBITORY ACTIVITY ON 5-REDUCTASE IN VITRO (1) The method of test

The test was carried out with reference to the method of J. Shimazaki et al [See Endocrinol, Japon., 18, 179 (1971)].

Male rat's prostate (4 g) was homogenized with its triple volume of 0.1M HEPES buffer (PH 7.4) including 0.25M cane sugar and was centrifuged at 3000 r.p.m. for 10 mins.

The precipitate was suspended into the buffer solution described above (10 ml), and the suspension was centrifuged at 3000 r.p.m. for 5 mins. The resulting precipitated was suspended in the buffer solution (3 ml) described above and was used as a sauce of enzyme.

A reaction mixture (total volume 0.1 ml) of [4-$C^{14}$]-testosterone (1.5 n mol, $1.5 \times 10^5$ cpm), NADPH (0.5 μmol), enzyme solution (0.03 ml) described above and several kinds of concentration of the compounds in the present invention was incubated for 60 mins at 37° C.

Enzyme reaction was quenched by addition of a mixture (0.4 ml) of chloroform and methanol (1:2), and the mixture was centrifuged at 2000 r.p.m. for 3 mins. The supernatant (50 μl) was spotted on silica gel thin layer plate. The spot on the plate was developed with a mixture of chloroform, methanol and acetic acid (99.2:0.6:0.2). Radioactivity of dihydrotestosteron generated on plate was measured by TLC scanner of radioautography and inhibitory ratio was calculated. The result is showed in the following table 1.

5α-reductase inhibitory activity

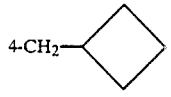

(I)

| Example No. | $(R^1)_n$ | $R^2$ | $R^3$ | 5α-reductase inhibitory activity $IC_{50}$ (μM) |
|---|---|---|---|---|
| 1 | 4-(CH$_2$)$_4$CH$_3$ | CH$_3$ | H | 0.20 |
| 1 (a) | 3-(CH$_2$)$_4$CH$_3$ | CH$_3$ | H | 0.16 |
| 1 (b) | 4-CH$_2$C(CH$_3$)$_3$ | CH$_3$ | H | 0.37 |
| 1 (c) | 4-CH$_2$CH(CH$_2$CH$_3$)$_2$ | CH$_3$ | H | 0.30 |
| 1 (d) | 4-CH$_2$CH(CH$_2$)$_2$CH$_3$ \| CH$_3$ | CH$_3$ | H | 0.34 |
| 1 (e) | 2-F-4-O(CH$_2$)$_4$CH$_3$ | CH$_3$ | H | 0.28 |
| 1 (f) | 4-S(CH$_2$)$_3$CH$_3$ | CH$_3$ | H | 0.43 |
| 1 (g) | 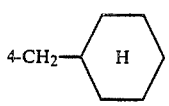 | CH$_3$ | H | 0.11 |
| 1 (h) | 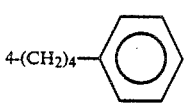 | CH$_3$ | H | 0.28 |
| 1 (i) | 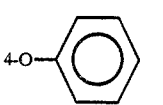 | CH$_3$ | H | 0.32 |
| 1 (j) | 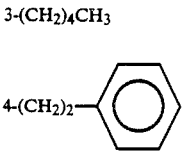 | CH$_3$ | H | 0.25 |
| 1 (k) | 3-(CH$_2$)$_4$CH$_3$ | H | CH$_3$ | 0.24 |
| 1 (l) | 4-(CH$_2$)$_2$-⌬ | H | CH$_3$ | 0.23 |

Compared compound:
Compounds group disclosed specifically in the Specification of the European Patent Publication No. 173516 and have measured inhibitory activity on 5 alpha-reductase practically — 2-5

(2) The result of test

The result of the test shows that all of the compounds of the present invention possess a strong inhibitory activity on 5α-reductase. A compared compound is the compound which its chemical structure is described specifically and possesses the greatest inhibitory activity on 5α-reductase among the compounds of which data on 5α-reductase are described concretely in the specification of the invention including the compounds of the present invention broadly (disclosed in Japanese Patent Kokai No. 61-126061 and referred to "the prior invention" hereinafter). It has been confirmed that inhibitony activities on 5α-reductase of the compounds of the present invention are from 4.4 to 18.2 times as strong as that of the compared compound. It can be unexpected that the compounds possessing such a great activity exist.

The compounds of the present invention possess a great inhibitory activity on 5-reductase and therefore are useful for prevention and/or treatment of disease resulted from the excess generation of dihydrotestosteron in mammals, especially human. Moreover, it was confirmed that the toxicity of the compounds of the present invention was very low and therefore they may be used as medicine sufficiently safely.

APPLICATION FOR THE PHARMACEUTICALS

For the purpose above described, the compounds of the present invention may normally by administered systemically (mainly in the case of prevention and/or treatment of prostatic hypertrophy) or partially (mainly in the case of prevention and/or treatment of alopecia and acne), usually by oral or parenteral administration.

The doses to be administered are determined depending upon age, body weight, symptom, the desired therapeutic effect, the route of administration, and the duration of the treatment etc. In the human adult, for the treatment and/or prevention of prostatic hypertrophy, the doses per person per dose are generally between 1 mg and 1 g, by oral administration, up to several times per day, and between 100 μg and 100 mg, by parenteral administration (preferably intravenous administration) up to several times per day.

In the human adult, for the treatment and/or prevention of alopecia and/or acne, the doses per person per dose are genrally between 10 μg and 50 mg, by dermal administration up to several times per day.

As mentioned above, the doses to be used depend upon various conditions. Therefore, there are cases in which doses lower than or greater than the ranges specified above may be used.

In the administration, the compounds of the present invention was administred as solid compositions, liquid compositions and other compositions for oral administration and injections, external compositions and suppositories etc. for parenteral administration.

Solid compositions for oral administration, include compressed tablets, pills, dispersible powders, capsules, and granules. In such compositions, one or more of the active compound(s) is or are, admixed with at least done inert diluent (lactose, mannitol, glucose, hydroxypropylcellulose, microcrystalline cellulose, starch, polyvinylpyrrolidone, magnesium metasilicate alminate etc.). The compositions may also comprise, as is normal practice, additional substances other than inert diluents: e.g. lurbricating agent (magnesium stearate etc.), disintegrating agents (cellulose calcium gluconate etc.), and assisting agent for dissolving (glutamic acid, aspertic acid etc.) stabilizing agent (lactose etc.).

The tablets or pills may, if desired, be coated with gastric or enteric material (sugar, gelatin, hydroxypropylcellulose or hydroxypropylmethylcellulose phthalate etc.).

Capsules include soft ones and hard ones.

Liquid compositions for oral administration include pharmaceutically-acceptable emulsions, solutions, suspensions, syrups and elixirs.

In such compositions, one or more of the active compound(s) is or are comprise in inert diluent(s) commonly used in the art (purified water, ethanol etc.).

Besides inert diluents, such compositions may also comprise adjuvants (wetting agents, suspending agents etc.), sweetening agents, flavouring agents, perfuming agents and preserving agents.

Other compositions for oral administration include spray compositions which may be prepared by known methods and which comprise one or more of the active compound(s).

Spray compositions may comprise additional substances other than inert diluents: e.g. stabilizing agents (sodium sulfite etc.), isotonic buffer (sodium chloride, sodium citrate, citric acid etc.).

For preparation of such spray compositions, for example, the method described in the U.S. Pat. Nos. 2,868,691 or 3,095,355 may be used.

Injections for parenteral administration include sterile aqueous or non-aqueous solutions, suspensions and emulsions. In such compositions, one or more of active compound(s) is or are admixed at least one of inert aqueous diluent(s) (distilled water for injection, physiological salt solution etc.) or inert non-aqueous diluent(s) (propylene glycol, polyethylene glycol, olive oil, ethanol, POLYSOLBATE 80 (registered trade mark) etc.).

Injections may comprise additional other than inert diluents: e.g. preserving agents, wetting agents, emulsifying agents, dispersing agents, stabilizing agents (lactose etc.), assisting agents such as assisting agents for dissolving (glutamic acid, aspertic acid etc.).

They may be sterilized, for example, by filtration through a bacteria-retaining filter, by incorporation of sterilizing agents in the compositions or by irradiation. They also be manufactured in the form of sterile solid compositions, for example, by freeze-drying, and which can be dissolved in sterile water or some other sterile diluents for injection immediately before used.

Other compositions for parenteral administration include liquids for external use, and endermic liniments (ointment etc.), suppositories and pessaries which comprise one or more of the active compound(s) and may be prepared by known methods.

Compositions for dermal administration, especially for the treatment and prevention of alopecia and acne, include liquids for external use such as lotion, tonic, spray, solution, suspension, emulsion and liniments such as ointment, gel, cream.

Such compositions may comprise one or more of active ingredient(s) and at least one of inert diluent(s), for example, distilled water, lower alcohols such as ethanol, higher alcohols such as cetanol, poly alcohols such as polyethylene glycol, propylene glycol, celluloses such as hydroxypropyl cellulose, animal or plant fats, vaseline, wax, silicone, plant oil such as olive oil, surfactants, zinc oxide etc.

Besides inert diluents, such composition may also comprise adjuvants (wetting agents, suspending agents, perfuming agents, preserving agents).

REFERENCE EXAMPLES AND EXAMPLES

The following reference examples and examples illustrate the present invention, but not limit the present invention.

The solvents in the parentheses show the developing or eluting solvents and the ratios of the solvents used are by volume in chromatographic separations.

REFERENCE EXAMPLE 1

3-(4-pentylphenyl)-2EZ-butenoic acid ethyl ester

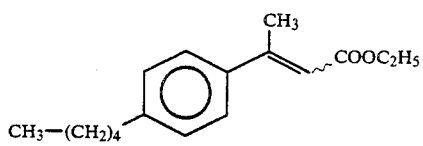

Sodium hydride (28.6 g, content: 63%) was suspended in tetrahydrofuran (1000 ml). Diethyl ethoxycarbonylmethylphosphonate (168 g) dissolved in tetrahydrofuran (500 ml) was added dropwise into the mixture with cooling in an ice-bath over 30 mins. 4-Pentylacetophenone (95 g) in tetrahydrofuran (500 ml) was added to the solution. The solution was stirred overnight at a room temperature and then refluxed at 8 hrs. Tetrahydrofuran was evoporated from the reaction mixture. Diluted hydrochloric acid was added to the residue. The acidic solution was extracted with ethyl acetate. The ertract was dried over magnesium sulfate and evaporated. The residue was purified by column chromatography on silica gel (n-hexane:ethyl acetate=99:1→98:2→95:5) to give the title compound (128 g) having the following physical data:

TLC; Rf 0.32 and 0.43 (n-hexane:ethyl acetate=10:1).

REFERENCE EXAMPLE 2

3-(4-penthylphenyl)-2E-butenoic acid

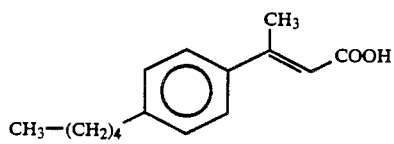

Ester (60.3 g: prepared in reference example 1) was dissolved in a mixture of methanol (1300 ml) and tetrahydrofuran (800 ml). An aqueous solution of sodium hydroxide (2N; 575 ml) was added to the solution. The solution was stirred at a room temperature for 1 hr and then at 50° C. for 1 hr. The reaction mixture was extracted with ether to remove the neutral substance. The aqueous layer was acidified with 6N hydrochloric acid. The acidic solution was dried over magnesium sulfate and then evaporated to give crude crystals. The crystals were recrystalized from n-hexane to give the title compound (32.7 g) having the following physical data:

TLC: Rf 0.40 (n-hexane:ethylacetate=2:1).

REFERENCE EXAMPLE 3

4-(2-nitrophenoxy)butanoic acid ethyl ester

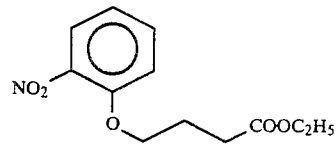

Sodium hydride (16.5 g, content: 62.4%) was suspended in N,N-dimethylformamide (500 ml). O-nitrophenol (60 g) dissolved in N,N-dimethylformamide (100 ml) was added dropwise into the mixture with stirring in ice-bath over about 20 mins. The mixture was stirred for 1 hr. at a room temperature.

4-bromobutanoic acid ethyl ester (84.2 g) dissolved in N,N-dimethylformamide (200 ml) was added to the mixture. The solution was stirred for 15 hrs at about 70° C. N,N-dimethylformamide was evaporated in vacuo. Ethyl acetate (800 ml) was added to the residue. The mixture was washed with a water and a saturated brine, dried over magnesium sulfate and evaporated. The residue was purified by column chromatography on silica gel (n-hexane:ethyl acetate=5:1→3:1) to give the title compound (77.3 g) having the following physical data:

TLC; Rf 0.35 (n-hexane:ethyl acetate=2:1).

REFERENCE EXAMPLE 4

4-(2-aminophenoxy) butanoic acid ehtyl ester

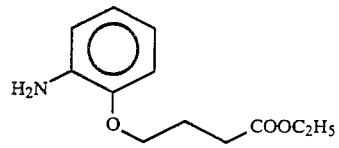

Nitro compound (77.0 g; prepared in reference example 3) dissolved in ethanol (500 ml) was added to palladium carbon (13.1 g, content: 10%) suspended in a mixture of chloroform (100 ml) and ethanol (500 ml). The mixture was stirred for 10 hrs at a room temerature under an atmosphere of hydrogen. The reaction mixture was filtered to remove the catalyst. The filtrate was evaporated to give a white solid (79 g).

The obtained solid was dissolved in ethyl acetate (1000 ml). A saturated aqueous solution of sodium bicarborate (500 ml) was added to the solution. The solution was stirred at a room temperature. The separated oily layer was washed with a saturated brine, dried over magnesium sulfate and evaporated. The residue was purified by column chromatography on silica gel (n-hexane:ethyl acetate:methylene chloride=90:5:5→70:15:15) to give the title compound (60.0 g) having the following physical data:

TLC: Rf 0.43 (n-hexane:ethyl acetate:methylene chloride=2:1:1).

REFERENCE EXAMPLE 5

4-[2-(4-pentyl-β-methylcinnamoylamino)phenoxy]-butanoic acid ethyl ester

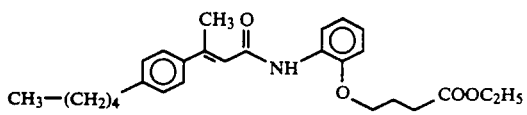

A mixture of butenoic acid derivatire (58 g; prepared in reference example 2) and oxalyl chloride (218 ml) was stirred for 1 hr at a room temperature. The obtained solution was evaporated to give the corresponding acid chloride. The acid chloride (obtained before) dissolved in methylene chloride (500 ml) was added dropwise into an amine (55.75 g; prepared in reference example 4) disolved in a mixture of methylene chloride (1500 ml) and pyridine (100 ml) in a ice-bath. The mixture was stirred for 2 hrs at a room temperature. The reaction mixture was poured into diluted hydrochloric acid. The separated oily layer was washed with a diluted hydrochloric acid, a diluted aqueous solution of sodium hydroxide, water followed by a saturated brine, dried over sodium sulfate and then evaporated to give the title compound (114.5 g) having the following physical data as crude products. The products was used in the following reaction without purification.

TLC; Rf 0.69 (n-hexane:ethyl acetate=2:1).

EXAMPLE 1

4-[2-(4-pentyl-β-methylcinnamoylamino)phenoxy]-butanoic acid

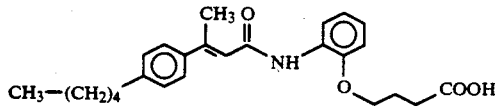

2N aqueous solution of sodium hydroxide (625 ml) was gradually added to the crude ethyl ester (114.5 g; prepared in reference example 5) dissolved in a mixture of methanol (1500 ml) and tetrahydrofuran (500 ml). The mixture was stirred for 2 hrs at a room temperature. The reaction mixture was evaporated. 2N hydrochloric acid (650 ml) was added to the residue. The acidic solution was extracted with ethyl acetate. The extract was washed with water, followed by a saturated brine, dried over magnesium sulfate and evaporated to give crude crystals (pale yellow). The crystals were recrystallized from a mixture of n-hexane and benzene (2:3) to give the title compound (87 g) having the following physical data:

m.p.: 111° C.;
TLC: Rf 0.54 (n-hexane:ethyl acetate=1:2);
NMR: δ8.45 (1H, m), 7.96 (1H, m), 7.41 (2H, d), 7.26 (2H, d), 6.96 (2H, m), 6.82 (1H, m), 6.28 (1H, m), 4.08 (2H, t), 2.60 (5H, m), 2.18 (2H, m), 1.61 (2H, m), 1.32 (4H, m), 0.90 (3H, t).

Hereinafter, using the corresponding acetophenone instead of 4-pentylacetophenone used in reference example 1, the compounds of the present invention shown in the following Table 2 were obtained by the same procedure as described in reference example 1~5 and example 1. Moreover, using the corresponding benzaldehyde instead of 4-pentylacetophenon used in reference example 1, or diethyl 1-ethoxycarbonyl-1-ethyl phosphonate instead of diethyl ethoxycarbonylmethyl phosphonate, the compounds of the present invention shown in the following Table 3 were obtained by the same procedure as described in reference example 1~5 and example 1.

TABLE 2

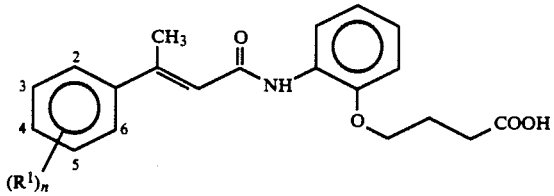

| Example No. | $(R^1)_n$ | Name | TLC | melting point or IR |
|---|---|---|---|---|
| 1 (a) | 3-(CH$_2$)$_4$CH$_3$ | 4-[2-(3-pentyl-β-methylcinnamoylamino)phenoxy]butanoic acid | Rf 0.23 (n-hexane: ethyl acetate = 2:1) | 86~87° C. |
| 1 (b) | 4-CH$_2$C(CH$_3$)$_3$ | 4-[2-(4-neopentyl-β-methylcinnamoylamino)phenoxy]butanoic acid | Rf 0.39 (n-hexane: ethyl acetate = 1:1) | 130.5~132° C. |
| 1 (c) | 4-CH$_2$CH(CH$_2$CH$_3$)$_2$ | 4-[2-{4-(2-ethylbutyl)-β-methylcinnamoylamino}phenoxy]butanoic acid | Rf 0.37 (n-hexane: ethyl acetate = 2:1) | 102~104° C. |
| 1 (d) | 4-CH$_2$CH(CH$_2$)$_2$CH$_3$ \| CH$_3$ | 4-[2-{4-(2-methylpentyl)-β-methylcinnamoylamino}phenoxy]butanoic acid | Rf 0.55 (n-hexane: ethyl acetate = 1:1) | 130.5~131° C. |
| 1 (e) | 2-F & 4-O(CH$_2$)$_4$CH$_3$ | 4-[2-(2-fluoro-4-pentyloxy-β-methylcinnamoylamino)phenoxy]butanoic acid | Rf 0.29 (n-hexane: ethyl acetate = 1:1) | 109~109.5° C. |
| 1 (f) | 4-S(CH$_2$)$_3$CH$_3$ | 4-[2-(4-butylthio-β- | Rf 0.28 | 122° C. |

TABLE 2-continued

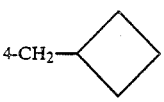

| Example No. | $(R^1)_n$ | Name | TLC | melting point or IR |
|---|---|---|---|---|
| | | methylcinnamoylamino)phenoxy] butanoic acid | (n-hexane: ethyl acetate = 2:1) | |
| 1 (g) | 4-CH$_2$-□ | 4-[2-(4-cyclobutylmethyl-β-methylcinnamoylamino)phenoxy] butanoic acid | Rf 0.40 (n-hexane: ethyl acetate = 1:2) | 128–129° C. |
| 1 (h) | 4-CH$_2$-⬡H | 4-[2-(4-cyclohexylmethyl-β-methylcinnamoylamino)phenoxy] butanoic acid | Rf 0.35 (n-hexane: ethyl acetate = 1:1) | 138.5–140° C. |
| 1 (i) | 4-(CH$_2$)$_4$-⬡ | 4-[2-{4-phenylbutyl)-β-methylcinnamoylamino}phenoxy] butanoic acid | Rf 0.25 (n-hexane: ethyl acetate = 2:1) | ν 3325, 3100–2300, 1710, 1640, 1610, 1530, 1450, 1255, 1180, 940, 740 cm$^{-1}$ |
| 1 (j) | 4-O-⬡ | 4-[2-(4-phenoxy-β-methylcinnamoylamino)phenoxy] butanoic acid | Rf 0.25 (n-hexane: ethyl acetate = 1:1) | 141.5–143° C. |

TABLE 3

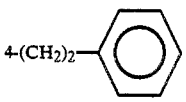

| Example No. | $(R^1)_n$ | Name | TLC | melting point or IR |
|---|---|---|---|---|
| 1 (k) | 3-(CH$_2$)$_4$CH$_3$ | 4-[2-(3-pentyl-α-methylcinnamoylamino)phenoxy] butanoic acid | Rf 0.22 (n-hexane: ethyl acetate = 1:1) | ν 3470, 3300–2300, 1715, 1670, 1605, 1530, 1450, 750 cm$^{-1}$ |
| 1 (l) | 4-(CH$_2$)$_2$-⬡ | 4-[2-(4-phenethyl-α-methylcinnamoylamino)phenoxy] butanoic acid | Rf 0.49 (ethyl acetate) | ν 3450, 3050–2800, 1718, 1670, 1600, 1525, 1450, 1290, 1260, 1220, 750 cm$^{-1}$ |

PREPARATION EXAMPLE

Preparation of tablets containing 4-[2-(4-pentyl-β-methylcinnamoylamino)phenoxy]-butanoic acid 4-[2-(4-pentyl-β-methylcinnamoyl)aminophenoxy]-butanoic acid (5 g), Cellulose calcium gluconate (disintegrating agent: 200 mg), Magnesium stearate (lubricating agent: 100 mg) and Microcrystaline cellulose (4.7 g) were admixed in conventional method and punched out to obtain 100 tablets each containing 50 mg of active ingredient.

What is claimed is:

1. A cinnamoylamide derivative of the formula:

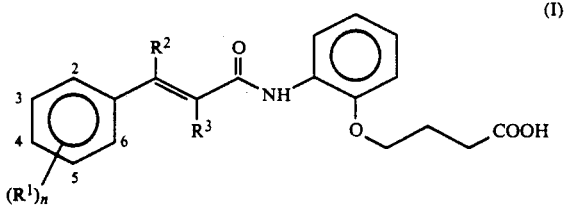

(I)

wherein, $R^2$ and $R^3$ each represents a hydrogen atom or methyl group with the proviso that
(i) when $R^2$ represents a methyl group and $R^3$ represents a hydrogen atom, and $(R^1)n$ represents a member selected from the group consisting of
4-cyclobutylmethyl group,
4-cyclohexylmethyl group, and
4-(4-phenylbutyl) group or
(ii) when $R^2$ represents a hydrogen atom and $R^3$ represents a methyl group, and $(R^1)n$ represents 4-phenethyl group,
or non-toxic salts thereof.

2. A derivative according to claim 1, wherein
(i) when $R^2$ represents a methyl group, $R^3$ represents a hydrogen atom, and $(R^1)n$ represents a member selected from the group consisting of
4-cyclobutylmethyl group and
4-cyclohexylmethyl group or
(ii) when $R^2$ represents a hydrogen atom, $R^3$ represents a methyl group, and $(R^1)n$ represents a 4-phenethyl group.

3. A derivative according to claim 2, wherein $R^2$ represents a methyl group, $R^3$ represents a hydrogen atom and $(R^1)n$ represents a 4-cyclobutylmethyl group.

4. A pharmaceutical composition for treating alopecia, acne or prostatic hypertrophy which comprises an effective amount of cinnamoylamide derivative of the formula (I) depicted in claim 1 or a non-toxic salt thereof, and pharmaceutically acceptable carrier and/or coating.

* * * * *